(12) United States Patent
Beesley

(10) Patent No.: US 7,105,822 B1
(45) Date of Patent: Sep. 12, 2006

(54) CHARACTERIZATION OF CLARITY AND COLOR ENHANCEMENT AGENTS IN GEMS

(75) Inventor: Casper R. Beesley, New York, NY (US)

(73) Assignee: American Gemological Laboratories, Inc., New York, NY (US)

(*) Notice: Subject to any disclaimer, the term of this patent is extended or adjusted under 35 U.S.C. 154(b) by 127 days.

(21) Appl. No.: 09/967,357

(22) Filed: Sep. 28, 2001

Related U.S. Application Data

(60) Provisional application No. 60/236,497, filed on Sep. 29, 2000.

(51) Int. Cl.
*G01J 5/02* (2006.01)

(52) U.S. Cl. ................... 250/341.1; 356/30

(58) Field of Classification Search ............. 250/341.1; 356/30
See application file for complete search history.

(56) References Cited

U.S. PATENT DOCUMENTS

| | | | | |
|---|---|---|---|---|
| 3,867,032 A | * | 2/1975 | Bruck | 356/30 |
| 5,835,200 A | * | 11/1998 | Smith et al. | 356/30 |
| 5,883,388 A | * | 3/1999 | Smith et al. | 356/30 |
| 6,515,738 B1 | * | 2/2003 | Barres et al. | 356/30 |
| 6,667,808 B1 | * | 12/2003 | Clermont et al. | 356/451 |

* cited by examiner

*Primary Examiner*—David Porta
*Assistant Examiner*—Shun Lee
(74) *Attorney, Agent, or Firm*—Milde & Hoffberg LLP

(57) ABSTRACT

Diffuse reflectance spectroscopy using near infrared and mid infrared radiation is used to detect the presence of organic chemical compounds in gems. Suitably, diffuse reflectance infrared Fourier transformation spectroscopy is employed to detect the presence of organic compounds in gems using mid infrared and near infrared radiation. The apparatus uses an integrating sphere or integrating cylinder with a probe that acts as both a source of near infrared radiation and a detector of reflected diffuse internal energy from the gem. Alternatively, the integrating sphere or integrating cylinder is replaced with a reflective fluid which surrounds the gem and causes total internal reflection.

3 Claims, 11 Drawing Sheets

ABSORBANCE

WAVENUMBER (cm-1)

CHARACTERIZATION OF CLARITY AND COLOR ENHANCEMENT AGENTS IN GEMS

This application claims the benefit of U.S. Provisional Patent Application No. 60/236,497, filed Sep. 29, 2000.

BACKGROUND OF THE INVENTION

1. Field of Invention

The present invention relates to gems and, more particularly, to a process for detecting the presence of organic compounds which have been used as enhancement/treatment agents to fill surface reaching fissures, fractures, pores and imperfections in gemstones.

The process of the present invention uses Near Infrared (NIR) and Mid Infrared (MIR) radiation, reflected diffuse energy and spectroscopic analysis to detect the presence of organic fillers.

2. Art Relating to the Invention

Gems are a category of minerals that exhibit a unique set of physical and optical characteristics that are reflected in their color, clarity, hardness, degree of transparency and dispersion. These attributes blend together with related properties to define the beauty, desirability and rarity that define a gemstone's desirability and market value. In most cases, with the exception of pearls and related organic material, gems are generally cut and polished for ornamental purposes. Natural materials can be replicated in the laboratory by various techniques that are typically referred to as laboratory grown or synthetic products. Because of the extreme geochemical conditions of gem material formation, structural issues at an atomic level and the methods of recovery, many gems contain surface reaching fissures, fracture systems and porosity. The presence of imperfections and blemishes can significantly decrease the value of a gem in the market place. For example, two of the most costly chromium-bearing gems, Ruby and Emerald, typically contain surface reaching fissures and fractures that impact on their value. It is a common practice in the jewelry industry to enhance a gem's appearance and subsequently its beauty, by filling these imperfections with foreign substances, thereby altering the appearance of the reflecting and visually distracting surface reaching fractures.

Organic compounds which are conventionally used to enhance the beauty of gems include oils, waxes, epoxy resins and other natural and synthetic resins. These organics are generally undetectable to the human eye. By selecting fillers or enhancement/treatment agents with optical characteristics similar to that of the gemstone, the effectiveness of the masking agent is increased. For example, a Colombian Emerald with a characteristic refractive index of 1.569–1.577 can effectively be altered by using EPON 828, an epoxy resin that has a similar refractive index of 1.573. This near match can create the illusion of significantly greater value. The improvement in appearance can make the difference between a salable and non-salable item and potentially increase the market value of the end product by thousands of dollars. Although commonly sold without disclosure of these additives, the Federal Trade Commission and other government agencies mandate full disclosure of all enhancement agents that are not permanent and ultimately affect the economic position of a consumer.

Infrared spectroscopy has been employed to examine gems in the past. Typically, the gem is placed in front of an infrared radiation source and a detector is positioned behind the gem to capture radiation that is transmitted through or emitted from the gem. The radiation source and the detector being in the same line of sight. Due to the scattering of the radiation, the captured radiation does not always provide an adequate "finger print" of the enhancement/treatment agents identity or indicate the quantity of the organic filler present.

Another method suggested for detecting organic compounds in gemstones has been Raman Spectroscopy. The Raman microprobe is a laser based analytical device that has been used to detect organic fissure filling, clarity enhancement agents. Althouh it offers good spatial resolution, it only analyses specific inclusions or points along a fracture and not the total gem simultaneously. The equipment is expensive and implementation of the technique is labor intensive and tedious. In addition, minerals that fluoresce, like ruby, are not good candidates for Raman analysis. Aggregate materials like turquoise, jade and pearl are equally problematic because of excessive signal scattering.

There is a need for a quick, simple means to detect the presence opf organic compounds in gemstones.

SUMMARY OF THE INVENTION

It has now been discovered that diffuse reflectance spectroscopy using infrared radiation can be used to effectively detect organic chemical compounds in gems. Thus, the process of the present invention determines whether an organic chemical compound has been used to fill the fractures, pores, or imperfections in a cut gemstone, rough (uncut) gem materials and porous materials like pearls.

Diffuse reflection spectroscopy, also referred to as diffuse reflectance spectroscopy, in accordance with the present invention, illuminates the sample with infrared radiation and collects reflected internal energy, optimizing the reflected diffuse internal energy, while minimizing the impact of specular reflected energy. Preferably, the radiation is diffuse. A transparent or translucent solid such as a gemstone reflects energy in several ways. Specular reflection energy is from radiation which is reflected directly off the surface of the sample. Reflected diffuse internal energy is from radiation that has penetrated the sample and has been reflected from within.

The process of the present invention analyzes the gem without damaging the gem and in a very short period of time, typically, less than one minute per sample. Conventional analysis for organic fillers as practiced in many gemological laboratories can require as much as two hours per sample, using current analytical techniques.

Applicant has found that near infrared (NIR) and mid infrared (MIR) range of radiation provides the best results for analyzing the presence of organics in a gem using diffuse reflectance spectroscopy. Unlike conventional infrared analysis, gemstone samples cannot be manipulated or destructively altered to accommodate the sample holding device. Typically, analytical labs prepare samples to accommodate the sample chamber. Fixed dimension liquid cells, or thin sections are commonly employed to analyze materials. Gems represent a non-standard analytical challenge. Each gem is typically cut for maximum weight and/or yield from a piece of uncut gem material (rough). The high cost of material commonly in the $5,000 to $25,000/ct range (5 carats=1 gram) for cut, high quality gem material dictates the configuration and shape variables of the final product. Since effective, non-destructive testing is essential, the sample presentation methods must present sufficient variability to accumulate the wide range of cutting formats or geometries of gemstones. Several illumination and analytical options based on diffuse reflectance spectroscopy is required to extend the measurement capabilities and range of organic filler detection.

The amount of organics in a carrier (gem material) can also affect the choice of diffused reflectance spectroscopy employed in the sampling process. Small amounts of filler or quantification of filler may necessitate an analysis of all light entering the gem by using a total internal reflection cell or its equivalent.

Also, the lighter in color the gem, the less radiation that is needed. A darker colored gem will need more radiation or illumination. Also, external or ambient light is preferably minimized or excluded during the process of the present invention.

The electromagnetic spectrum is arbitrarily divided in different bands or wavelength regions. One of these spectrum bands is the infrared spectrum band. The infrared spectrum band lies between the red end of visible light at approximately 0.75 µm and extends to the 1000 µm region. It has been found that near infrared (NIR) and the mid infrared (MIR) region are the most useful for the identification of organic enhancement or alteration agents in various inorganic hosts. As is known, different chemical bonds absorb radiation differently and exhibit unique vibrational patterns based on the energy absorbed. These molecular vibrational patterns can be detected, analyzed and quantified against known standards to determine the presence and amount of different chemical compounds. Also, as is known the sensitivity of this analysis can be greatly improved by the use of Fourier transformation. Additionally, by cooling the sample, the spectrum can be sharpened.

In using diffuse reflectance spectroscopy to detect the presence of organic chemical compounds in gems, applicant has found that Fourier transformation can be effectively employed to analyze the detected energy. Fourier transformation is a conventional means to manipulate data and is used in the present invention in a conventional manner.

Fourier transformation has been applied to diffuse reflectance spectroscopy which employs infrared radiation and such a process is called diffuse reflectance infrared Fourier transformation spectroscopy (DRIFTS). Instruments that use DRIFTS are conventional.

There are a plurality of apparati that can be used in accordance with the present invention. One such apparatus is a device which amounts to a single fiber-optic probe that has both a radiation source conduit and a detector conduit for collecting diffuse energy that focuses at the tip of the probe. To operate the probe, the sample is touched with the probe and illuminated with infrared radiation. The radiation is then absorbed by the gem and reflected by the gem as diffuse internal energy. This reflected diffuse internal energy is captured by the detector portion of the probe and then analyzed by the computer controlled detector array. Such NIR probes are conventional. Alternatively, the apparatus comprises a pedestal inside an integrating sphere (hollow sphere coated internally with a reflective diffusing material like SPECTRALON or diffuse gold coating). The NIR and MIR radiation is diffused and uniformly reflected from the walls of the sphere into the gemstone. The gemstone is mounted on the probe and the detection probe is mounted directly below the gemstone. Preferably, a transparent aluminum oxide sphere focuses the emerging energy onto the entrance of the fiber optic detection probe that is channeling the reflected diffuse internal energy to the detector array.

Suitable apparati that employ DRIFTS and can be used in accordance with the present invention include NICOLET MAGNA IR Series 760 and 860; BOMEN FT-NEAR IR Analysis; BIORAD FTIR 60A FTIR; NICOLET MAGNA Series 860; PERKIN ELMER LAMBDA 1C Spectrometer; and FOSS NIR System each with a diffuse reflector device (integrating sphere) from Spectratec, Pike Technologies, and Lapsphere. Such devices are operated in a conventional manner.

NIR probes are also conventional pieces of equipment which are operated in a conventional manner in order to accomplish the present invention. Suitable NIR probes can be obtained from Foss NIR System of Silver Spring, Md. and Nicolet Instrument Corporation of Madison, Wis.

Gems which can be subjected to the process of the present invention include all natural and synthetic gems such as diamonds, rubies, emeralds, sapphires, jade, turquoise, alexandrite, chalcedony, and pearl, as well as other gems that exhibit surface reaching fissure, fractures or porosity. Gems which can be subject to the present invention include not only those which have been cut and polished, but also those that are rough, i.e. not cut or polished. The main prerequisite for analysis is the presence of an "organic window" or non-absorbing areas in the spectral regions where organic materials exhibit characteristic spectral peaks.

Organic chemical compounds which can be detected by the present invention include both natural and synthetic compounds which have been used to enhance or alter the appearance of a gem. Such compounds include oils, waxes, and various natural and synthetic resins. Oils which can be detected by the present invention include, among others, cedar wood oil, Thai red oil, Canadian balsam, mineral oil, Indian dyed joban oil, clove stem oil, sesame oil and synthetic oil of wintergreen. Waxes and other solid/semi-solid fillers which can be detected by the present invention include shellac, carnauba and paraffin. Resins, polymers and prepolymers which can be detected by the present invention include PALMA, epoxy resin, EPON 828, CIBA-GEIGY 6010, OPTICON 224, as well as hardened and unhardened alternative resins.

The present invention can detect both single and multiple organic compounds.

BRIEF DESCRIPTION OF THE DRAWINGS

These and other aspects of the present invention may be more fully understood by reference to one or more of the following drawings.

DETAILED DESCRIPTION OF THE INVENTION

Figure 1:
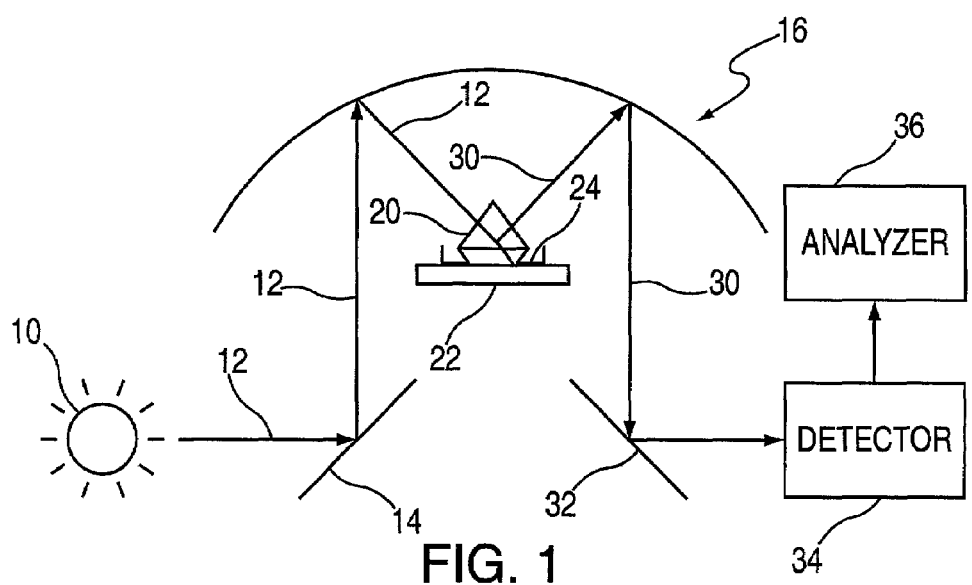
FIG. 1 illustrates a conventional DRIFTS device as used in the process of the present invention.

As illustrated in FIG. 1, a conventional DRIFTS device is illustrated which can be employed in the present invention. Source 10 is a source of infrared radiation. Source 10 emits radiation beam 12 which is deflected off a mirror 14 and directed to parabolic mirror 16 which, in turn, directs beam 12 to gem 20. Gem 20 is contained on base 22 and in reflective cup 24. Gem 20 reflects both specular and internal energy while cup 24 reflects internally transmitted energy, all of which are energy 30. The reflected energy is captured by parabolic mirror 16 and reflected down to mirror 32 which, in turn, reflects it to detector 34 and detector 34 captures reflected diffuse internal energy. Analyzer 36 then performs a Fourier transformation on the captured data of the reflected energy in order to determine the presence or absence of organic chemical compounds. An analyzer 36 is suitably a conventional computer with the necessary software.

Figure 2:
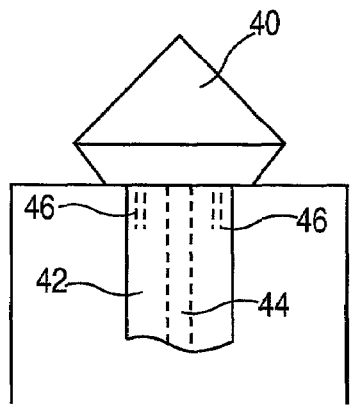
FIG. 2 illustrates a NIR probe with a gem on top.
Figure 2:
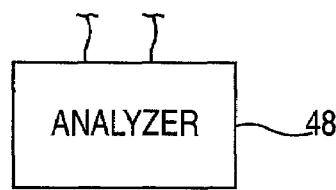

FIG. 2 illustrates the present invention for use with a probe. As depicted in FIG. 2, gem 40 is placed on top of probe 42. Probe 42 has a center of fiber-optic core 44 which emits NIR radiation. Only reflected diffuse internal energy from gem 40 is captured by detectors 46 and then transmitted to analyzer 48.

Figure 3:
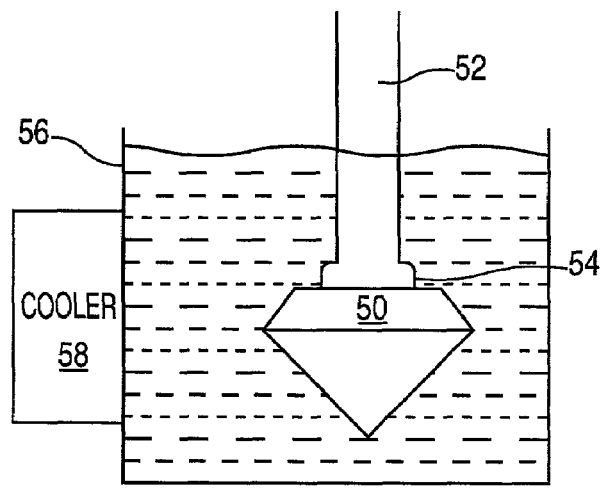
FIG. 3 illustrates a NIR probe having a gem attached thereto and immersed in a reflective solution.

FIG. 3 illustrates another embodiment of the apparatus for use in the present invention wherein a total internal reflection immersion cell is employed. In this embodiment, gem 50 is held onto probe 52 by means of a holding device, shown as sealed vacuum cup 54. Probe 52 with attached gem 50 is then immersed into reflective bath 56. Bath 56 causes total internal reflection of NIR radiation. Thus, the detectors in probe 52 obtain reflected diffuse internal energy from gem 50. Any radiation which would normally have passed outward through gem 50 is reflected back into gem 50 because bath 56 acts as a mirror to NIR radiation. In order to improve the spectrum, cooling unit 58 can be employed to cool bath 56 and gem 50. Such cooling units are conventional and operated in a conventional manner to cool bath 56.

Stabilizing the temperature of the measuring environment is important for consistent instrumental results. However, spectral features can be altered and/or enhanced by the application of temperature to the sampling environment. Cooling samples can in many instances accentuate spectral features. A thermocouple controlled temperature alteration device like a thermoelectric cooler and supplemental heating element placed on the outside of the total internal reflection immersion cell provide uniform cooling and heating of the sample by surrounding the sample with a uniform temperature controlled fluid environment. Alternatively, the immersion cell can be placed in a secondary chamber in order to be cooled with liquid nitrogen.

One of skill in the art can also use any type of reflective solutions that produce total internal reflection or apply an outside coating directly on the gem surface to produce total internal reflection. Reflective solutions and coating such as metal coatings include gold, silver, or any material that has an adjusted index so as to cause total internal reflection.

Figure 3A:
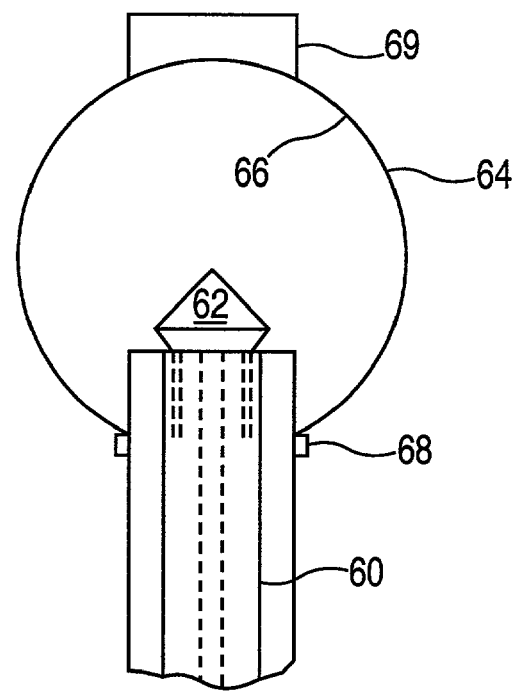
FIG. 3A is another embodiment of the present invention.

FIG. 3A illustrates another embodiment where probe 60 with gem 62 is placed inside removable hollow sphere 64. Sphere 64 has a diffuse reflective material 66 coating its inside surface. Probe 60 is identical to probe 42. Removable sphere 64 rests on stop 68 and is removable with handle 69.

Figure 3B:
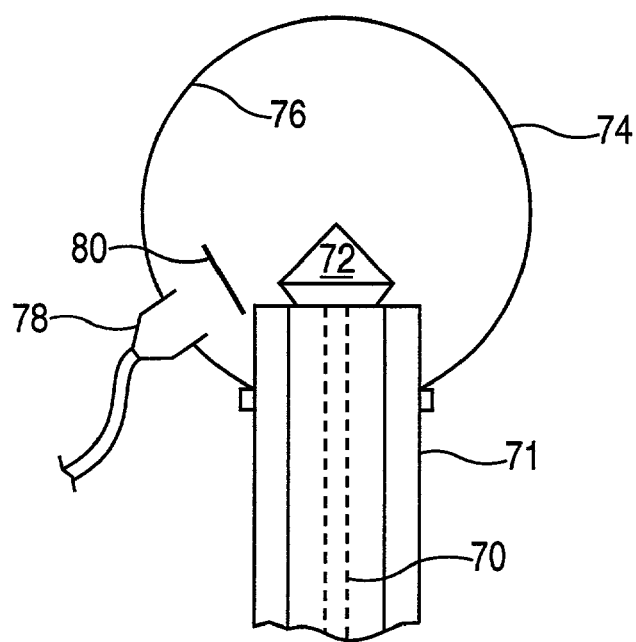
FIG. 3B is another embodiment of the present invention.

FIG. 3B illustrates another embodiment where IR detector channel 70 which leads to a detector is mounted in probe 71 on which gem 72 is mounted and placed inside hollow sphere 74 with diffuse reflective coating 76 therein. Sphere 74 has IR source 78. Baffle 80 avoids the radiation directly hitting gem 72 and insures that diffuse radiation is used.

Suitable diffuse reflective coatings for spheres 64 and 74 are diffuse gold coatings, SPECTRALON®, and other suitable diffuse reflective coatings normally used in integrating spheres.

Suitable instruments for this process include LPM-040-SL and LPM-040-IG Laser Power Measurement Spheres manufactured by Labsphere of North Sutton, N.H.

Figure 3C:
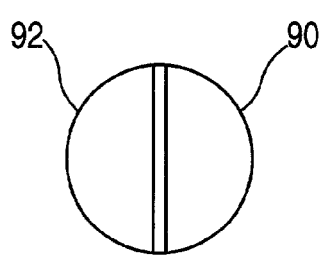
FIG. 3C is a top view of a probe in accordance with the present invention.

An alternative to probe 42, 52 or 60 is a split probe in which one half of the probe is a detector and the other half of the probe is an IR source. A top view of such a split probe is shown in FIG. 3C wherein channel 90 leads to a detector and channel 92 leads to a radiation source.

Figure 3D:
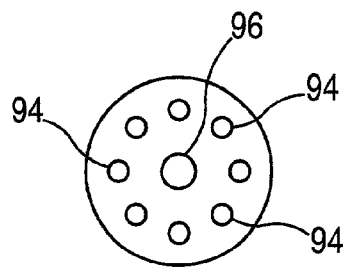
FIG. 3D is a top view of another probe in accordance with the present invention.

FIG. 3D illustrates a top view of another probe configuration in accordance with the present invention with multiple channels 94 leading to a detector and channel 96 provides radiation from a source.

Figure 3E:
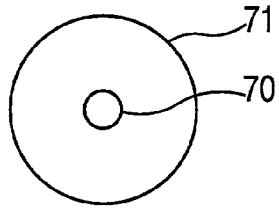
FIG. 3E is a top view of yet another probe in accordance with the present invention.

FIG. 3E illustrates a top view of the probe of FIG. 3B.

Figure 3F:
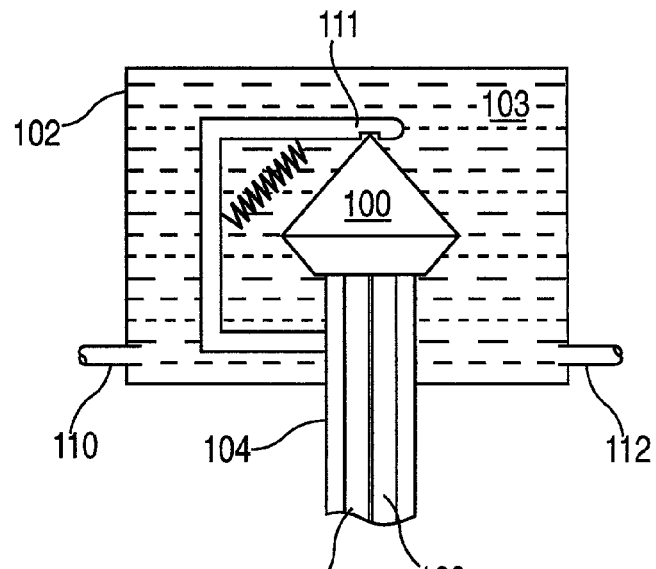
FIG. 3F is a side view of another embodiment of the device ilustrated in FIG. 3.

FIG. 3F is a side view of another total internal reflection immersion cell for immersing gem 100 in container 102 of reflective fluid 103. Probe 104 is similar to the one shown in FIG. 3C with radiation channel 106 and detector channel 108 such that it acts as both an illuminator and a detector. Container 102 has inlet and exit ports 110 and 112 to allow fluid 103 to be filled and drained between tests. C-clamp 110 has a spring load top for holding gem 100 in place on probe 104 during testing. Fluid 103 can be liquid or a gas which provides total internal reflection to gem 100.

Figure 3G:
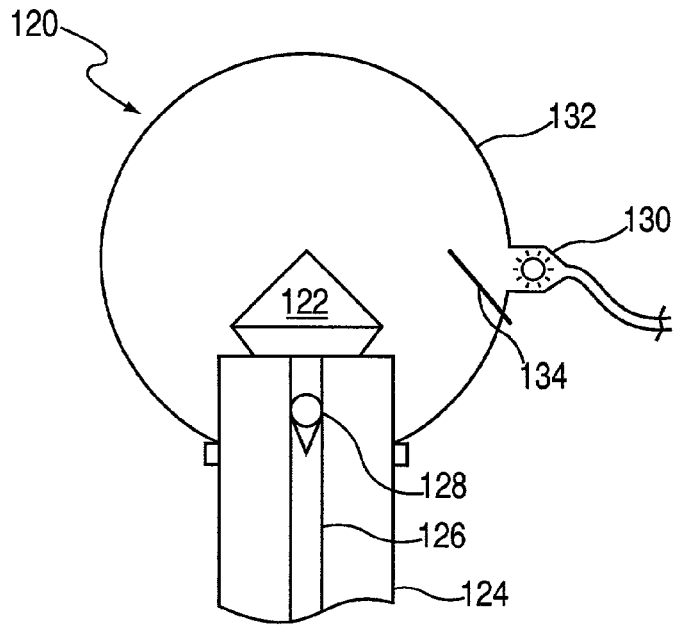
FIG. 3G is a side view of a device in accordance with the present invention that employs a focusing sphere.

FIG. 3G illustrates a device 120 in accordance with the present invention wherein gem 122 sits on probe 124. Channel 126 to the detector has aluminum oxide focusing sphere 128. IR source 130 is mounted in sphere 132 and baffled by baffle 134 to cause diffuse IR radiation throughout sphere 132. The inside wall of sphere 132 has a diffuse reflective coating.

Figure 3H:
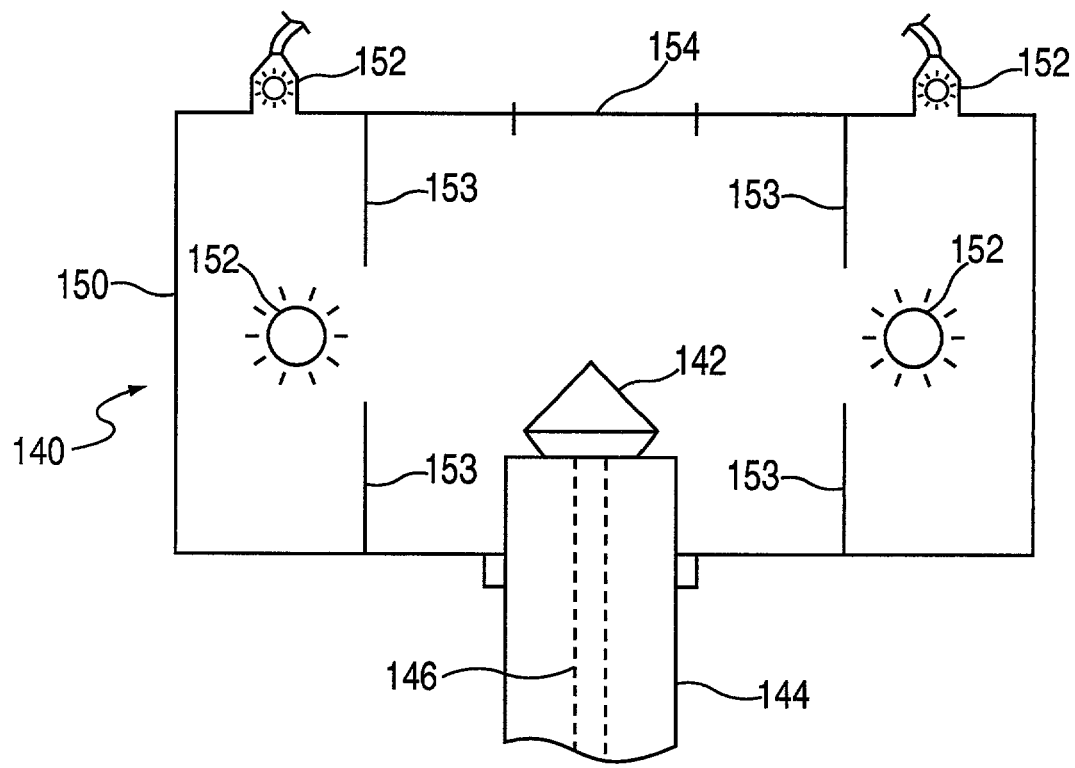
FIG. 3H is a side view of a device wherein an integrating cylinder is used.
Figure 3I:
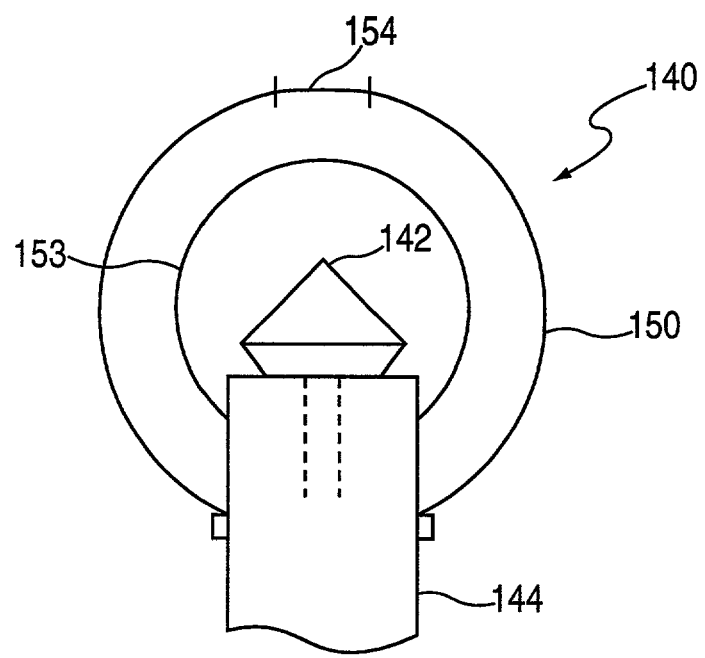
FIG. 3I is an end view of the integrating cylinder in FIG. 3H.

FIGS. 3H and 3I illustrate yet another device 140 in accordance with the present invention. Device 140 has gem 142 mounted on probe 144. Probe 144 has channel 146 to detector (similar to the device in FIG. 3E). Device 140 has integrating cylinder 150 with a plurality of IR radiation sources 152 each of which has baffle 153 for generating diffuse IR radiation in cylinder 150. Cylinder 150 has its inside walls coated with a diffuse reflective material similar to the integrating spheres illustrated in FIGS. 3A, 3B and 3G. The advantage to device 140 is that multiple IR sources are employed. IR source 152 face blank walls, not each other. Also, working with a flat, rectangular exterior of cylinder 150 provides advantages. Port 154 provides access to cylinder 150.

It should be noted that in the device of FIGS. 3A, 3B and 3G, it is preferred to have the gem at or near the center of the sphere or cylinder for best results.

These and other aspects of the present invention may be more fully understood by reference to one or more of the following examples.

Example 1

This example illustrates using near infrared (NIR) and a probe to detect the presence of epoxy in an emerald. Two emeralds were analyzed, one contained a small amount of epoxy, the other contained no epoxy. Both gems were approximately 5 mm in diameter.

Figure 4:
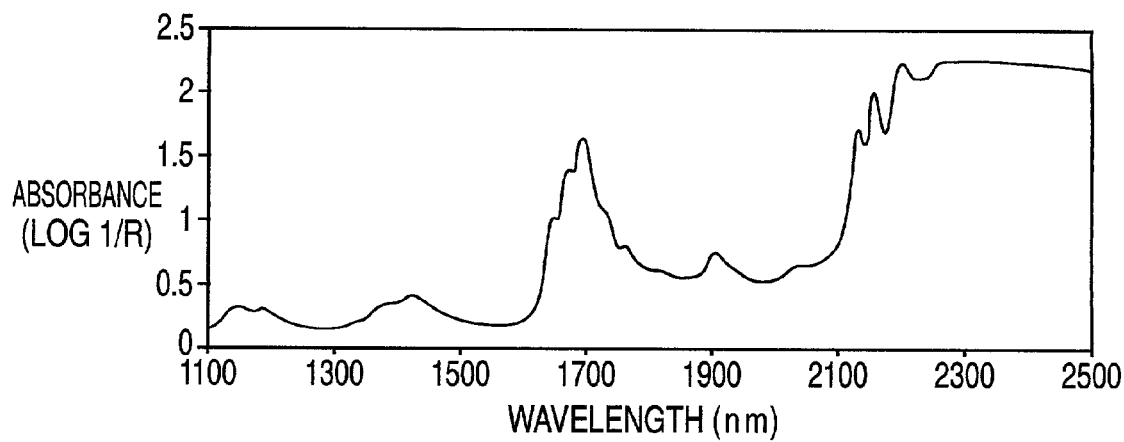
FIG. 4 illustrates a NIR spectra of pure epoxy resin.
Figure 5:
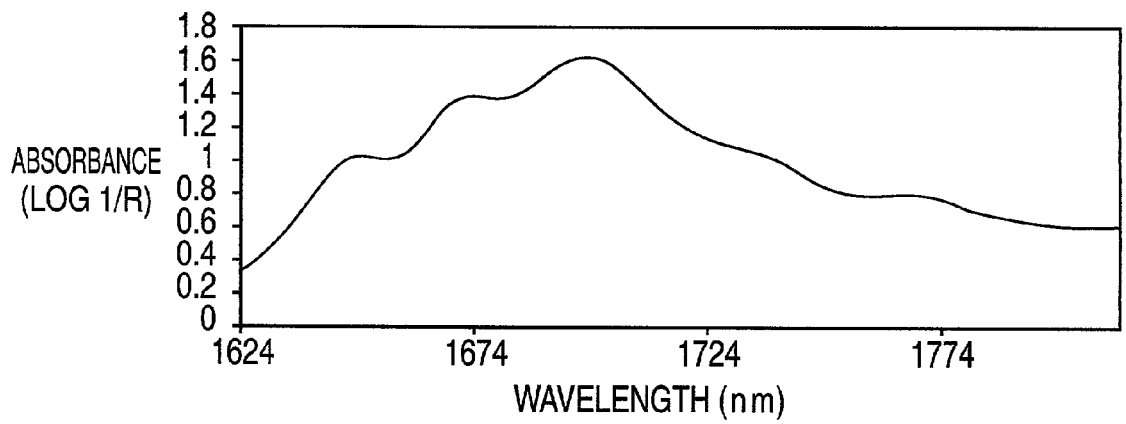
FIG. 5 illustrates the absorbance of pure epoxy resin in the C-H first overtone region from FIG. 1.

As indicated in FIG. 4, a pure epoxy sample has a strong absorption, around 1700 nm. Peaks appeared at approximately 1648, 1670, 1698 nm (see FIG. 5) and correspond to first overtone absorptions of C-H anticipated for epoxy (and not anticipated for emerald).

Figure 6:
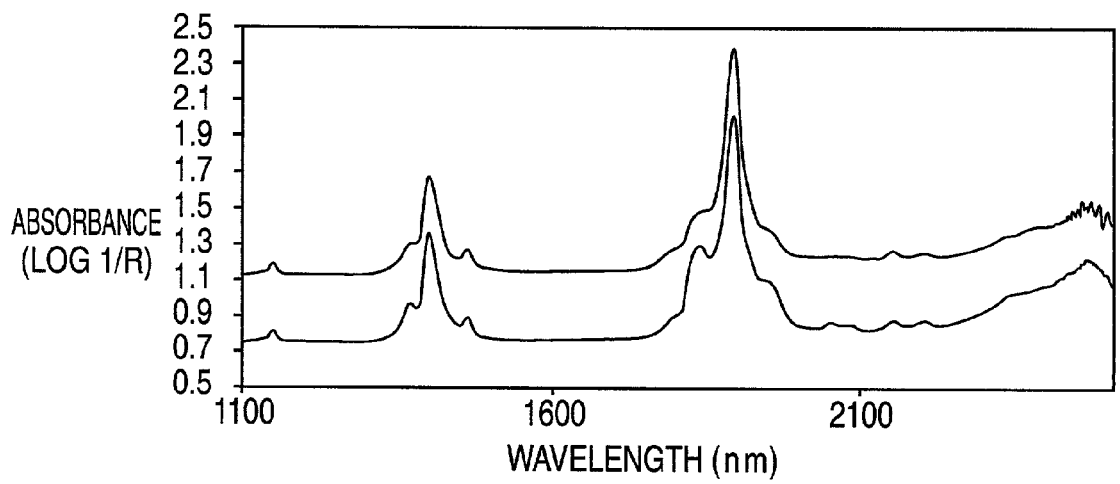
FIG. 6 illustrates the NIR absorbance spectra of an emerald sample containing no epoxy resin and an emerald sample containing an epoxy resin.

Absorbance spectra of the two emeralds are shown in FIG. 6. Although there are some differences (baseline and peak shape), no significant differences are seen at this scale in the region associated with strong epoxy absorbance.

Figure 7:
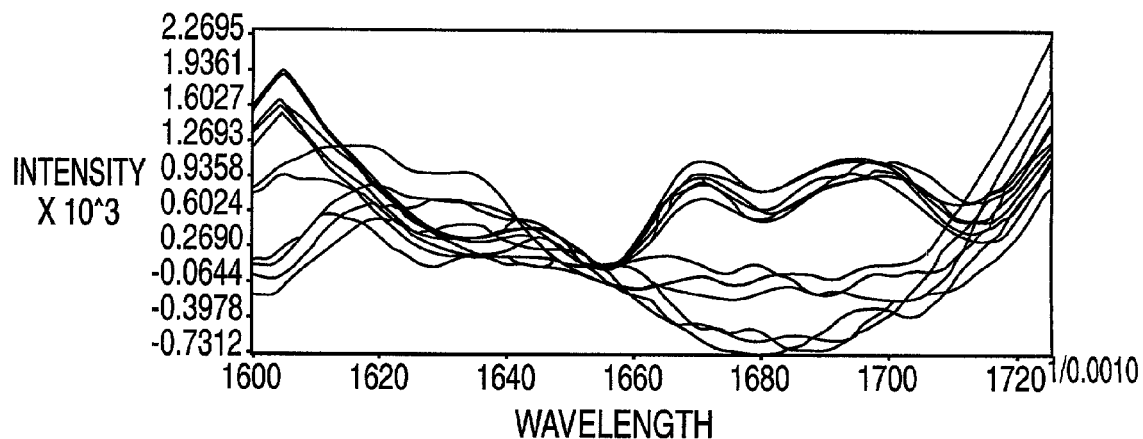
FIG. 7 illustrates the spectra for both the emerald containing epoxy resin and the emerald containing no epoxy resin of FIG. 6.

In order to verify the presence or absence of epoxy in the spectra of the emeralds, two different mathematical treatments were evaluated. The first was a detrend treatment that consisted of a first order detrend correction (determine the best line through the data points, then subtract that line from the spectrum) from 1600–1730 nm, followed by a baseline correction to offset spectra to zero absorbance at 1654 nm, followed by a 10 point box car smooth. The resulting spectra are shown in FIG. 7.

Figure 8:
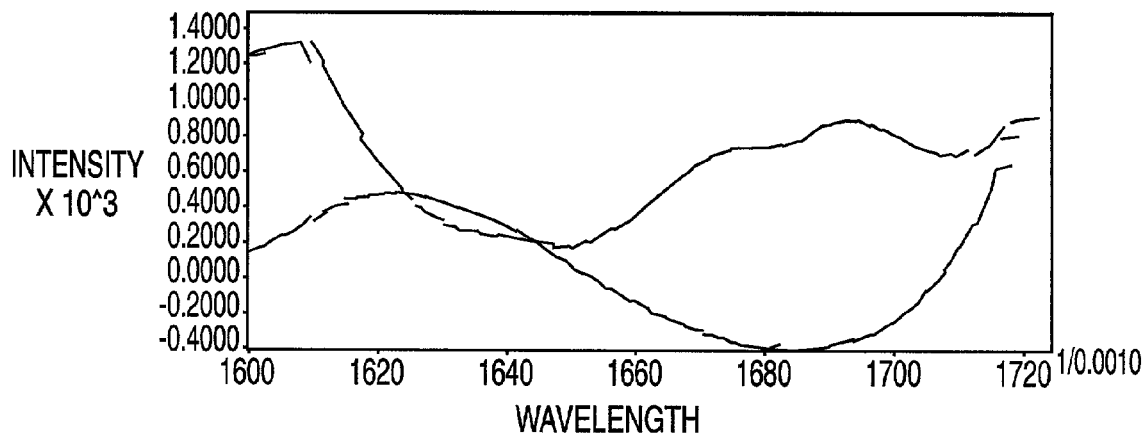
FIG. 8 illustrates the average spectra for the emerald with epoxy resin and the clean emerald of FIG. 7.

Clear differences due to the epoxy absorbance can be seen in these spectra at approximately 1696, 1670 and 1644 nm. To further clarify the plots, all spectra of the same sample were averaged and the results are shown in FIG. 8.

Figure 9:
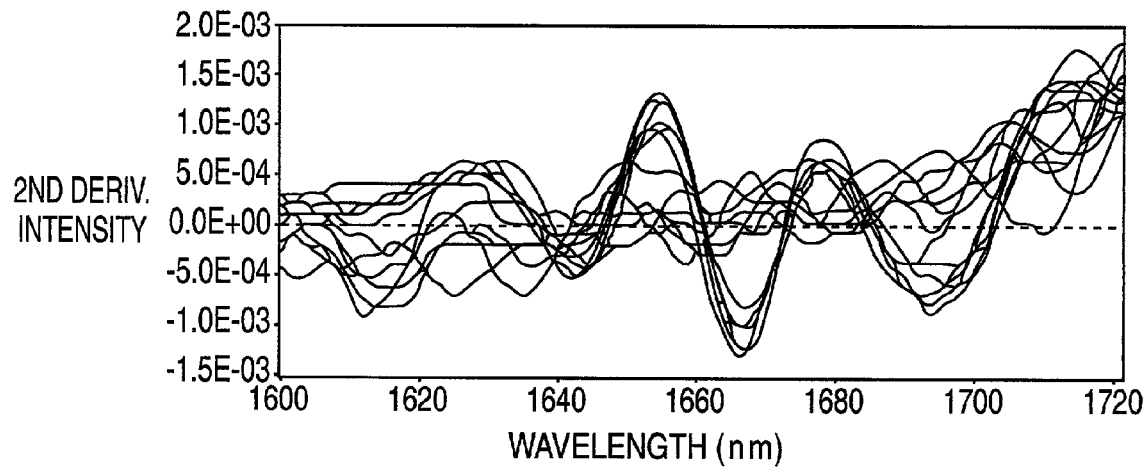
FIG. 9 illustrates the second derivative of the spectra for the emerald with epoxy resin and without epoxy resin of FIG. 8.

As an alternative, second derivatives were generated from the raw spectra. Second derivative math treatments are commonly used in NIR since it eliminates baseline variations while enhancing band resolution. Second derivative plots are shown in FIG. 9. The maxima are inverted in this math treatment. Again, absorbances due to epoxy can clearly be seen (1696, 1668, 1644 nm) in the individual spectra.

Figure 10:
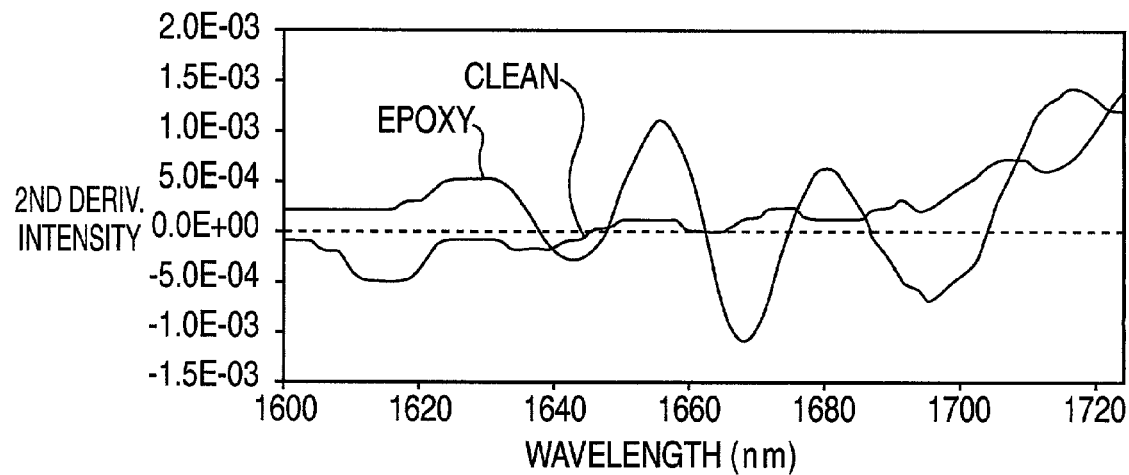
FIG. 10 illustrates the average spectra for the emerald with epoxy resin and the clean emerald of FIG. 9.

As before, individual plots were averaged to further enhance the results and these spectra are shown in FIG. 10.

As can be seen, diffuse reflection using NIR allowed for the detection of the organic, compound (epoxy) in the emerald.

The NIR analysis was conducted in a conventional manner using conventional equipment. Specifically, the following technique was employed for this example and some of the following examples.

PTFE beads were added to the liquid sample (epoxy, oils) in order to effect sufficient reflectance for a useful spectrum. The spectra for the liquid sample was acquired with a RAPID CONTENT ANALYZER (RCA) (Foss NIR Systems, Silver Spring, Md.), which consisted of a model 6500 monochromator and a Rapid Content Module (both Foss NIR Systems). The dispersed light from a tungsten-halogen source is brought to the sample compartment by means of a fiber-optic bundle (420 fibers, each 200 µm diam). This light then passes through the bottom of the vial (approximately 25 mm diam) containing the liquid sample and PTFE beads and is then reflected back into the detector array of the Rapid Content Module, which consists of four PbS detectors and four Si detectors for collection of near-IR and visible spectra, respectively. Although transmission measurements through cuvettes were possible, use of this PTFE bead method allowed the use of disposable vials. This facilitated the handling of viscous samples.

Solid samples (wax and gems) were analyzed with the RCA (described above), SMARTPROBE ANALYZER (Foss NIR Systems), and/or INTACT TABLET ANALYZER (Foss Systems). Whenever sample size permitted, gems were analyzed with all three analyzers in order to facilitate comparison of their spectra under different measurement conditions. Analysis of gems by the RCA consisted of simply centering each gem on the sampling area above the detectors. The SMARTPROBE ANALYZER consists of a model 6500 monochromator and a stainless steel fiber-optic bundle reflectance probe with 8-mm-diam sapphire window. The probe consists of two collinear fiber-optic bundles. Each bundle is 2 m long and is fabricated with 210 optic fibers (200 µm fiber diameter). One bundle transmits light from the exit slit of the monochromator to the sample. The reflected light from the sample is collected by the return fibers and is brought back to the analyzer for analysis by both a Si (400–1100 mm) and PbS (1100–2500 mm) detector. Gems were measured by securing the probe in a vertical configuration (window facing up), placing the samples on the probe tip window, and positioning a light shield over the sample probe tip.

The INTACT TABLET ANALYZER consists of a Model 6500 monochromator and an Intact Table transmission module. The light from the exit slit of the monochromator passes through a fiber-optic bundle composed of 420 optic fibers (fiber diameter=200 µm, is transmitted by the sample, and finally is collected on an InGaAs detector (600–1900 nm).

Each spectrum consists of 32 scans acquired at approximately 10 nm bandwidth, regardless of analyzer used. The gem samples were repositioned several times in order to optimize spectra. Digitized spectra were acquired and manipulated with the use of VISION software (Version 2.21) (Foss NIR Systems) or transferred to other data management software for processing.

Example 2

This example illustrates using NIR diffuse reflective spectroscopy and a probe to detect the presence of epoxy in turquoise.

Figure 11:
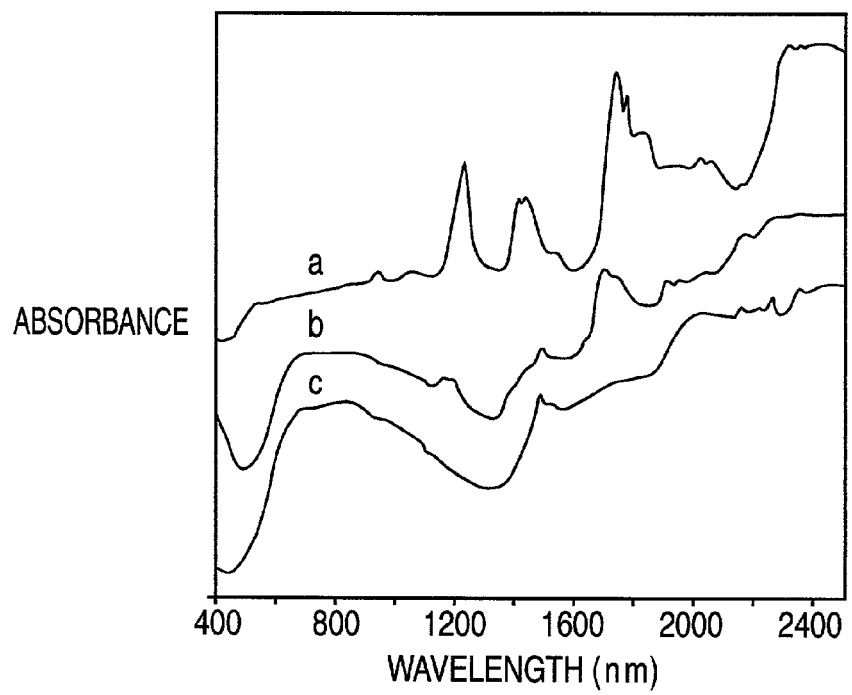
FIG. 11 illustrates the NIR spectra of pure epoxy resin, turquoise treated with epoxy resin, and untreated turquoise.

Turquoise beads were analyzed, one epoxy treated and one untreated. Both were tested according to Example 1 above. FIG. 11 illustrates epoxy spectra a, treated turquoise (turquois treated with epoxy) spectra b, and untreated turquoise spectra c.

Figure 12:
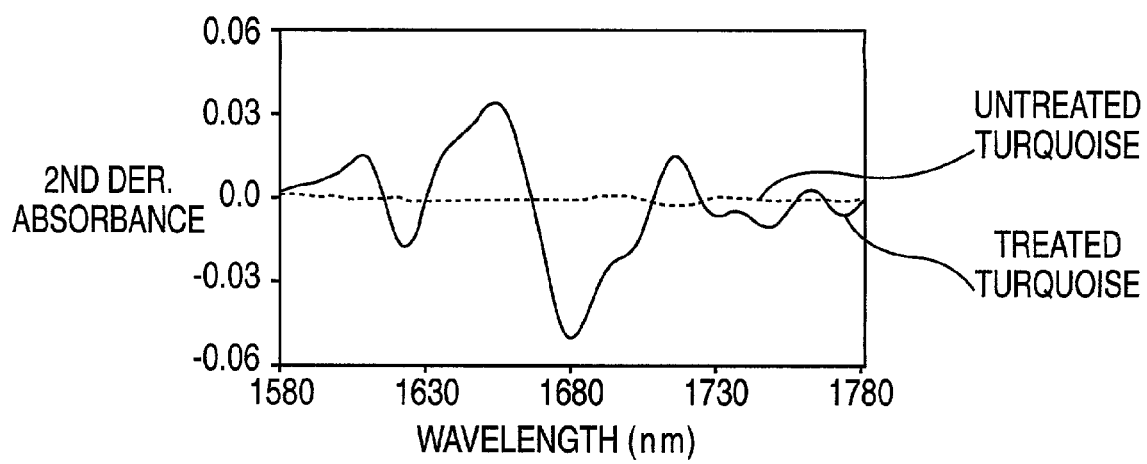
FIG. 12 illustrates the second derivative of the treated and untreated turquoise of FIG. 11.

FIG. 12 illustrates the second derivation spectra between 1580 and 1780 nm (where the C-H stretching overtones occur) for both the treated and untreated turquoise.

These tests were run in accordance with the procedure and equipment of Example 1 above.

As can be seen, the presence of the epoxy is detected.

Example 3

This example illustrates using NIR diffuse reflectance spectroscopy and a probe to detect the presence of epoxy in emeralds, different than the sample used in Example 1 above.

Two emeralds were analyzed, one epoxy treated and one untreated. Both were tested according to Example 1 above.

Figure 13:
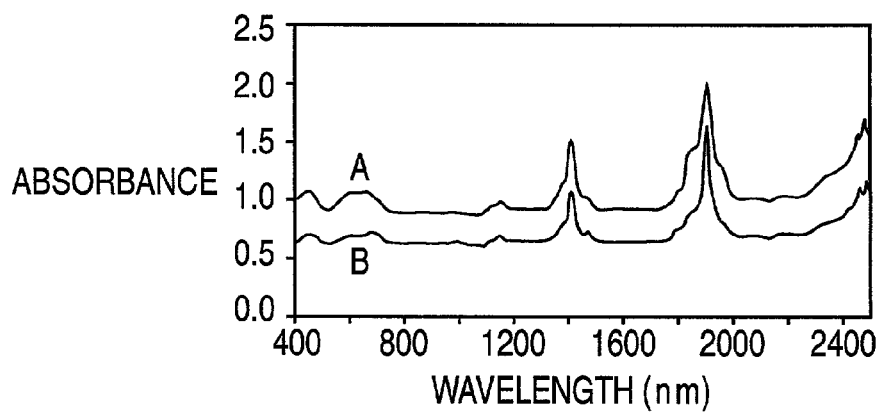
FIG. 13 illustrates an NIR spectra for emeralds, one which has been treated with epoxy resin and one which has been untreated.

FIG. 13 illustrates treated emerald spectra A, and untreated emerald spectra B.

Figure 14:
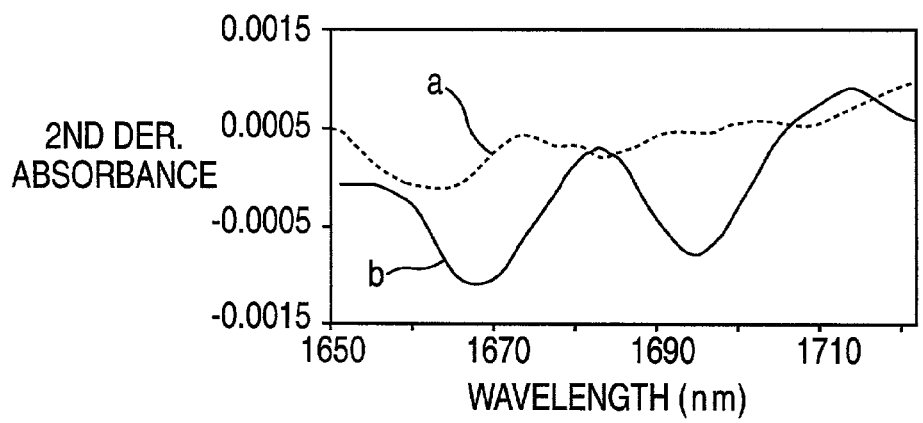
FIG. 14 illustrates the second derivative of FIG. 13 showing the treated and untreated emerald.

FIG. 14 illustrates the second derivation spectra between 1600 and 1750 nm (where the C-H stretching overtones occur) for both the untreated a and treated emeralds b.

These tests were run in accordance with the procedure and equipment of Example 1 above.

Example 4

This example illustrates using NIR diffuse reflectance spectroscopy and a probe to detect the presence of Thai red oil in rubies.

Figure 15:
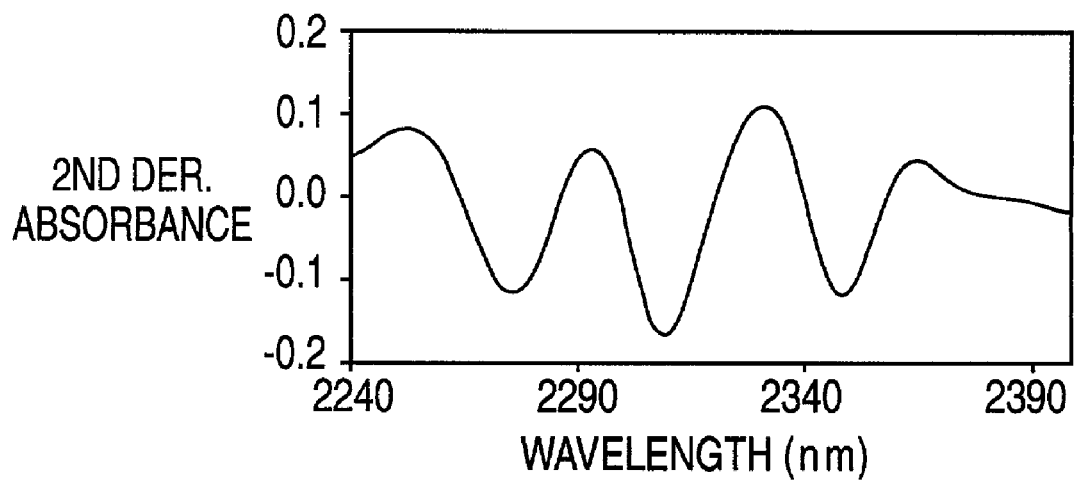
FIG. 15 illustrates an NIR spectra for pure Thai red oil.
Figure 16:
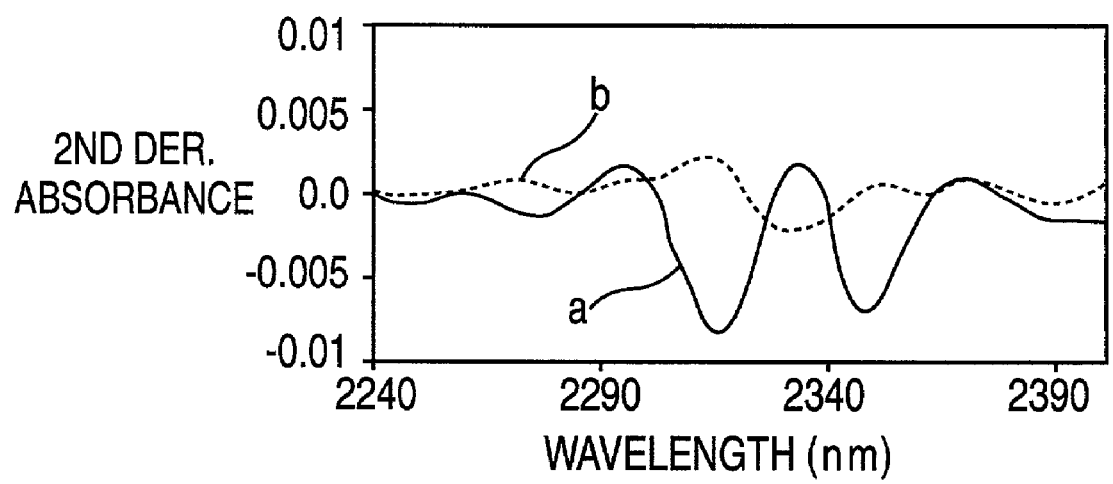
FIG. 16 illustrates an NIR spectra for treated and untreated rubies.

FIG. 15 illustrates the spectra for Thai red oil. FIG. 16 illustrates the second derivation spectra for a ruby treated with Thai red oil, curve a; and a clean, untreated ruby, curve b.

These tests were run in accordance with the procedure and equipment of Example 1 above.

As can be seen, the present invention allows for detection of the oil.

Example 5

This example illustrates using the DRIFTS technique to detect the presence of organic fillers in emeralds.

Figure 17:
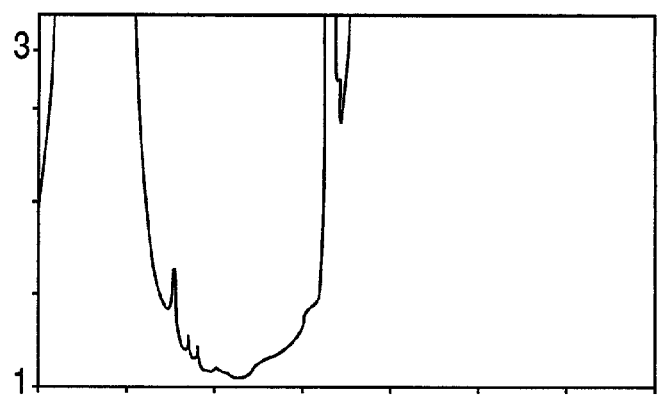
FIG. 17 illustrates a DRIFTS spectra for a clean emerald.
Figure 18:
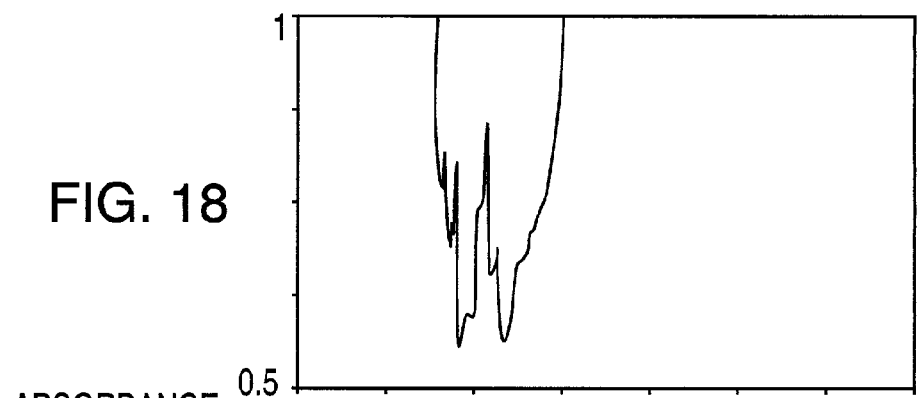
FIG. 18 illustrates a DRIFTS spectra for an emerald treated with epoxy resin.
Figure 19:
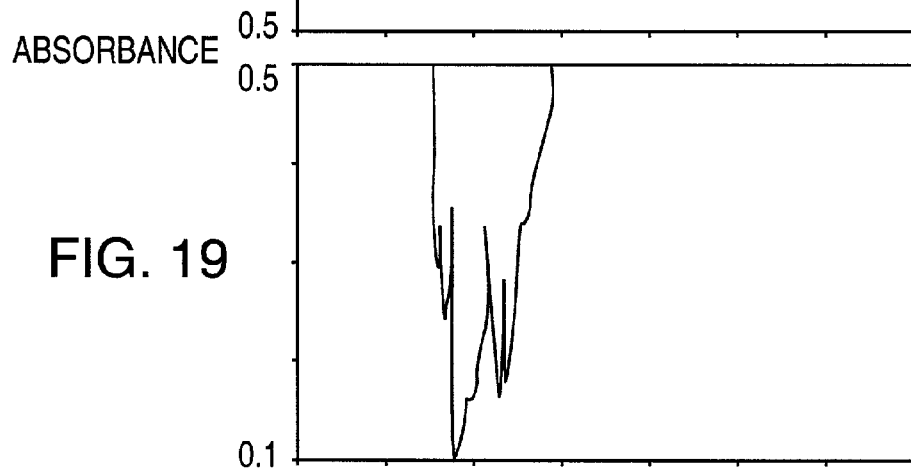
FIG. 19 illustrates a DRIFTS spectra for an emerald treated with a wax.
Figure 20:
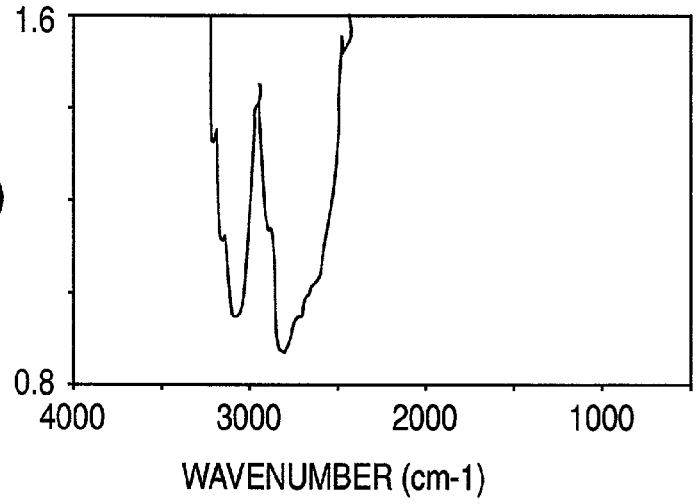
FIG. 20 illustrates a DRIFTS spectra for an emerald with an oil.

FIG. 17 illustrates the DRIFTS spectra for a clean, natural 0.58 ct. Columbian emerald. FIG. 18 illustrates the DRIFTS spectra for a 0.69 ct. emerald treated with an epoxy to fill the fractures. FIG. 19 illustrates a DRIFTS spectra for a 1.32 ct. emerald treated with wax. FIG. 20 illustrates a DRIFTS spectra for a 2.86 ct. emerald treated with an unknown oil approximately 20 years ago.

The C-H stretch band which determines the presence of an organic is around a wavelength of 2600 to 3000 $cm^{-1}$.

As can be seen, even small amounts of organic filler can be detected by the DRIFTS technique. In fact, the intensity of the C-H stretch band is a way to identify the type of organic filler.

The procedure and equipment used to conduct the DRIFTS analysis was conventional and similar to the device in FIG. 1. Specifically, the infrared windows made of potassium bromide were purchased from Aldrich. The infrared spectra of epoxy resin, oil and wax samples, the enhancers, were obtained using a NICOLET MAGNA-IR 750 spectrometer with a DTBS detector. The gem samples were analyzed using the same spectrometer equipped with a Spectra-Tech (Sheldon, Conn.) Baseline Diffuse Reflectance accessory. The accessory includes macro sampling cups made of polished stainless steel. The background was taken as a single-beam spectrum collected from an empty cup. After the alignment of the instrument and the accessory, the gem samples were placed in a macro sampling cup and inserted through the sample slide to the center of the accessory and infrared data were then collected. The position of the gem in the sampling cup was changed several times in order to maximize the C-H stretching bands. For larger samples which cannot be inserted directly using the sample slide, the alignment mirror was removed temporarily from its optimized position so a large entrance was available for the sample slide. After the gem sample was placed in the macro sampling cup and inserted to the center, the alignment mirror was returned to its optimized position and the data were then collected. All data were collected at 4 $cm^{-1}$ resolution. Each spectrum was a result of 32 coadds, collected from 4000 to 500 $cm^{-1}$. The data collected from the NICOLET computer were manipulated with the use of OMNIC FT-IR software or transferred to a PC for processing.

Example 6

This example illustrates using the DRIFTS technique to detect the presence of cedarwood oil in a ruby.

Figure 21:
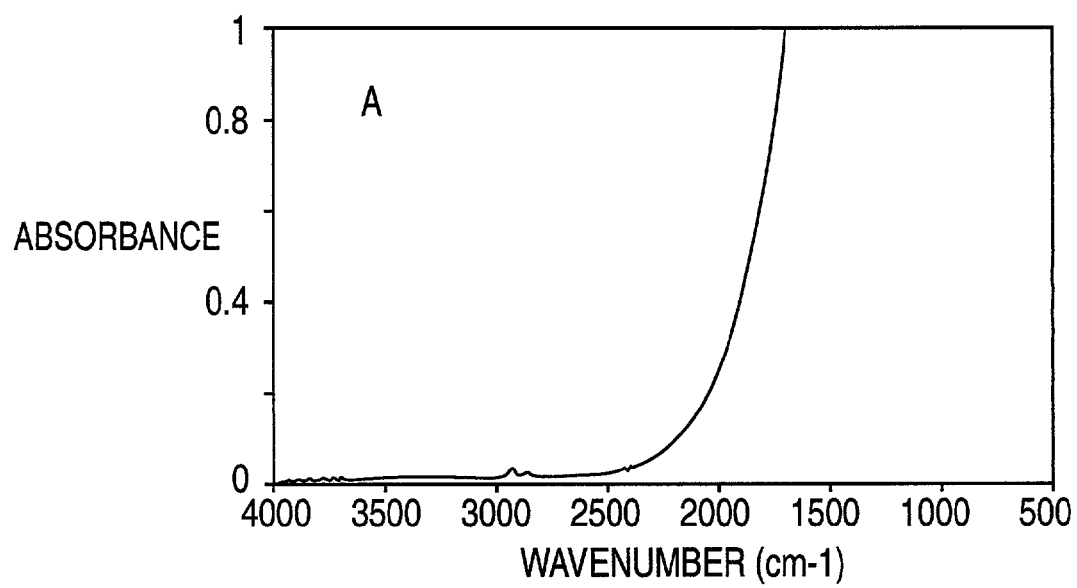
FIG. 21 illustrates a DRIFTS spectra for a clean ruby.
Figure 22:
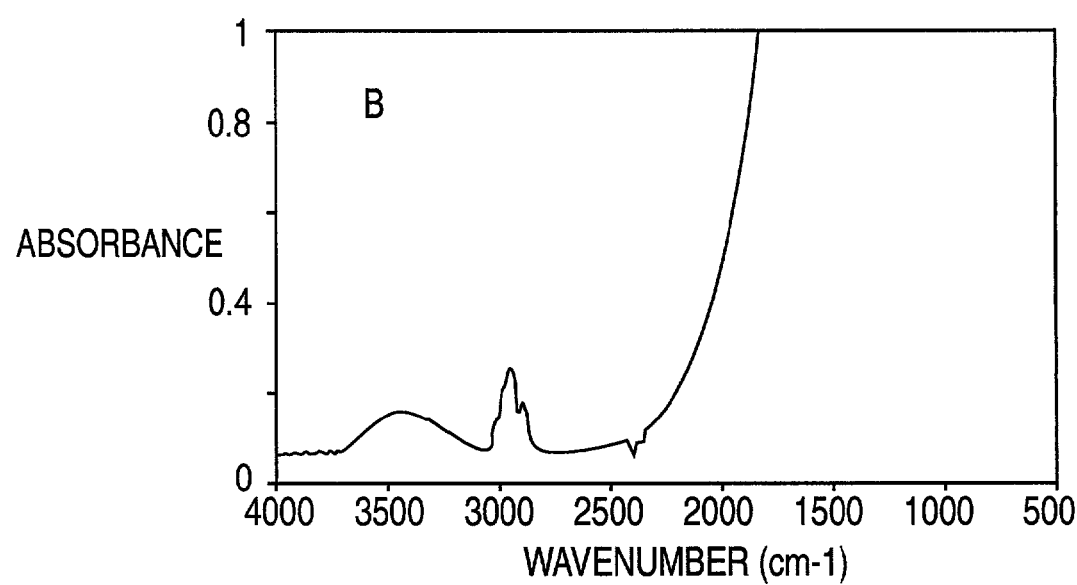
FIG. 22 illustrates a DRIFTS spectra for a ruby treated with cedarwood oil.

FIG. 21 illustrates the DRIFTS spectra for a clean, natural 1.22 ct. ruby from Thailand. FIG. 22 illustrates the DRIFTS spectra for a 9.34 ct. ruby that has been treated with cedarwood oil.

The DRIFTS technique used herein was the same as Example 5 above.

It will be understood that the claims are intended to cover all changes and modifications of the preferred embodiments of the invention herein chosen for the purpose of illustration which do not constitute a departure from the Spirit and scope of the invention.

What is claimed is:

1. A process for detecting one or more organic compounds in a gem comprising:
    touching a gem with a probe, said probe having a radiation source conduit for illuminating said gem with near infrared irradiation and a detection conduit for collecting reflected diffuse internal energy from said gem;
    coating said gem with a metallic reflective coating when illuminating said gem with near infrared radiation from said probe; and
    collecting and analyzing reflected diffuse internal energy from said gem to detect of an organic compound is present in said gem.

2. The process of claim 1 wherein said gem is a diamond, ruby, emerald, sapphire, jade, turquoise, pearl, chalcedony or alexandrite.

3. The process of claim 1 wherein said organic compound is oil, wax, resin, polymer or prepolymer.

* * * * *